(12) United States Patent
Liu et al.

(10) Patent No.: US 10,580,147 B2
(45) Date of Patent: *Mar. 3, 2020

(54) GPU-BASED SYSTEM FOR PERFORMING 2D-3D DEFORMABLE REGISTRATION OF A BODY ORGAN USING MULTIPLE 2D FLUOROSCOPIC VIEWS

(71) Applicant: Broncus Medical Inc., San Jose, CA (US)

(72) Inventors: Yixun Liu, Mountain View, CA (US); Lav Rai, Sunnyvale, CA (US); Henky Wibowo, Cupertino, CA (US)

(73) Assignee: Broncus Medical Inc., San Jose, CA (US)

( * ) Notice: Subject to any disclaimer, the term of this patent is extended or adjusted under 35 U.S.C. 154(b) by 111 days.

This patent is subject to a terminal disclaimer.

(21) Appl. No.: 15/888,825

(22) Filed: Feb. 5, 2018

(65) Prior Publication Data

US 2018/0240245 A1  Aug. 23, 2018

Related U.S. Application Data

(63) Continuation of application No. 15/060,582, filed on Mar. 3, 2016, now Pat. No. 9,886,760.

(Continued)

(51) Int. Cl.
*G06T 7/30* (2017.01)
*A61B 6/03* (2006.01)
(Continued)

(52) U.S. Cl.
CPC .............. *G06T 7/30* (2017.01); *A61B 6/032* (2013.01); *A61B 6/12* (2013.01); *A61B 6/4441* (2013.01); *A61B 6/466* (2013.01); *A61B 6/487* (2013.01); *A61B 6/488* (2013.01); *A61B 6/5205* (2013.01); *A61B 6/5235* (2013.01); *A61B 6/547* (2013.01);
(Continued)

(58) Field of Classification Search
CPC ..................... G06T 7/30; G06T 11/008; G06T 2207/10124; G06T 2207/10121; G06T 2207/30061; G06T 2211/428; A61B 6/547; A61B 6/5235; A61B 6/5205; A61B 6/488; A61B 6/487; A61B 6/466; A61B 6/4441; A61B 6/12; A61B 6/032; A61B 6/4476; A61B 6/0492; A61B 6/582

See application file for complete search history.

(56) References Cited

U.S. PATENT DOCUMENTS

2009/0052757 A1* 2/2009 Khamene ............. A61B 6/5235
382/131
2015/0030227 A1* 1/2015 Liang .................... G06T 11/006
382/131

(Continued)

OTHER PUBLICATIONS

Saxena et al., A parallel gpu algorithm for mutual information based 3d nonrigid image registration, springer, 2010.*

*Primary Examiner* — John B Strege
(74) *Attorney, Agent, or Firm* — Richard Batt

(57) ABSTRACT

Systems and methods for assisting a physician in a medical intervention comprises performing a 2D-3D deformable registration, and more particularly, performing a 2D-3D registration based on multiple live 2D fluoroscopic views, and implemented on a multi-core processing framework such as a Graphics Processing Unit.

17 Claims, 5 Drawing Sheets

Related U.S. Application Data

(60) Provisional application No. 62/128,885, filed on Mar. 5, 2015.

(51) Int. Cl.
*A61B 6/12* (2006.01)
*A61B 6/00* (2006.01)
*G06T 11/00* (2006.01)
*A61B 6/04* (2006.01)

(52) U.S. Cl.
CPC ........... *G06T 11/008* (2013.01); *A61B 6/0492* (2013.01); *A61B 6/4476* (2013.01); *A61B 6/582* (2013.01); *G06T 2207/10121* (2013.01); *G06T 2207/10124* (2013.01); *G06T 2207/30061* (2013.01); *G06T 2211/428* (2013.01)

(56) References Cited

U.S. PATENT DOCUMENTS

| | | | | |
|---|---|---|---|---|
| 2015/0201910 | A1* | 7/2015 | Zhao | A61B 10/04 600/424 |
| 2016/0012592 | A1* | 1/2016 | Chou | G06T 7/35 382/131 |
| 2016/0148380 | A1* | 5/2016 | Otomaru | G06T 7/33 382/294 |

\* cited by examiner

GPU-BASED SYSTEM FOR PERFORMING 2D-3D DEFORMABLE REGISTRATION OF A BODY ORGAN USING MULTIPLE 2D FLUOROSCOPIC VIEWS

CROSS-REFERENCE TO RELATED APPLICATIONS

This application is a Continuation of U.S. patent application Ser. No. 15/060,582, filed Mar. 3, 2016, which claims priority to U.S. Provisional Patent application No. 62/128,885, filed Mar. 5, 2015 and is incorporated by reference.

BACKGROUND OF THE INVENTION

Intra-operative poses of the lung of a patient may be computed from 2D live fluoroscopic images. The intra-operative poses can assist a physician in various medical procedures performed in the lung. For example, the pose information may be used to guide an instrument to a region of interest in the lung.

Computing the pose from the live 2D fluoroscopic images, however, is not straightforward. A challenge arises because the live 2D fluoroscopic images are missing information along the projection direction. Hence, the 2D fluoroscopic images need to be aligned with a preoperatively acquired 3D CT to provide volumetric anatomical information, which leads to the 2D-3D rigid registration.

2D-3D rigid registration has been performed using various techniques. See, for example, Otake, Y.; Armand, M.; Armiger, Robert S.; Kutzer, M. D.; Basafa, E.; Kazanzides, P.; Taylor, R. H., Intraoperative Image-based Multiview 2D/3D Registration for Image-Guided Orthopaedic Surgery: Incorporation of Fiducial-Based C-Arm Tracking and GPU-Acceleration, Medical Imaging, IEEE Transactions on, vol. 31, no. 4, pp. 948,962, April 2012. See also, Gao, Gang et al., Registration of 3D trans-esophageal echocardiography to X-ray fluoroscopy using image-based probe tracking, Medical Image Analysis, Volume 16, Issue 1, 38-49.

A challenge to performing 2D-3D rigid registration, however, is the high number of computations. 2D-3D rigid registration is computationally intense. Various techniques to speedup computations have been attempted. For example, one technique involves accelerating the Digitally Reconstructed Radiograph (DRR). Otake, Y.; Armand, M.; Armiger, Robert S.; Kutzer, M. D.; Basafa, E.; Kazanzides, P.; Taylor, R. H., Intraoperative Image-based Multiview 2D/3D Registration for Image-Guided Orthopaedic Surgery: Incorporation of Fiducial-Based C-Arm Tracking and GPU-Acceleration, Medical Imaging, IEEE Transactions on, vol. 31, no. 4, pp. 948,962, April 2012. Gao, Gang et al., Registration of 3D trans-esophageal echocardiography to X-ray fluoroscopy using image-based probe tracking, Medical Image Analysis, Volume 16, Issue 1, 38-49

However, despite speeding up the registration, the accuracy established by the rigid 2D-3D rigid registration is reduced because of the patient's non-rigid motion between 3D image acquisition and 2D image acquisition. In particular, the motion of the lung arising from the patient's repositioning, breathing, and beating heart introduces inaccuracies in the rigid registration.

To estimate the lung deformation, 2D-3D deformable registration is needed. For example, Su et al. presented a 2D-3D deformable registration method for lung intervention. (Su P, Yang J, Lu K, Yu N, Wong S T, Xue Z, A fast CT and CT-fluoroscopy registration algorithm with respiratory motion compensation for image-guided lung intervention, IEEE Trans Biomed Eng. 2013 July; 60(7):2034-41, TBME. 2013). In Su et al., the deformation in the transversal plan was modeled as a 2D Bspline and the deformation along the z direction was regularized by a smoothing term. Since the control points only move in the 2D plane, this method simplifies the 2D-3D registration to a 2D-2D registration problem.

Khamene et al. performed the non-rigid registration in 2D space for the alignment between the DRR and the fluoroscopic image and then back projected to 3D space. (Ali Khamene, Oliver Fluck, Shmuel Aharon, Deformable 2D-3D Registration, U.S. Pat. No. 8,184,886 B2, Date of Patent: May 22, 2012). See also U.S. Pat. No. 8,184,886 to Khamene et al., describing a method for deformable 2D-3D registration.

The above mentioned methods are based on intensity and simplify the 2D-3D deformation problem to a 2D-2D deformation problem. This reduces the degrees of freedom and computation complexity, but undesirably results in two issues: (1) the "overlapping" anatomical structures in 2D image are deformed as one "layer" and therefore the deformation may not capture the "independent" 3D motion of the structures and (2) the 2D-2D deformation model does not allow for a previously occluded/out-of-camera-view structure to appear which may happen as part of an actual 3D deformation. This reduces the accuracy of the 2D-2D deformation approach. Additionally, none of the above described methods use multiple 2D views "simultaneously" to determine a consistent 3D deformation field which gives a more accurate result.

Rivest-Henault et al. presented another 2D-3D deformable registration based on a feature instead of the intensity. The vessel centerlines were automatically extracted from 2D fluoroscopic images and the centerlines served the calculation of the mismatch in the cost function. (Rivest-Henault, D.; Sundar, H.; Cheriet, M., Nonrigid 2D/3D Registration of Coronary Artery Models With Live Fluoroscopy for Guidance of Cardiac Interventions, Medical Imaging, IEEE Transactions on, vol. 31, no. 8, pp. 1557,1572, August 2012). This method appears to address alignment of the blood vessels. However, Rivest-Henault does not provide a solution to the more complicated task, namely, an alignment of the 2D-3D data for an entire or complete lung.

Chou et al. presented another method to perform 2D-3D deformable registration. Chou et al. employed machine learning to build the mapping from the 3D deformation profile to the 2D DRR in the training stage, and then based on the distance between the test DRR and the training DRR, weighted the deformation. (Chen-Rui Chou, Stephen Pizer, Real-Time 2d/3d deformable registration using metric learning, MCV'12 Proceedings of the Second international conference on Medical Computer Vision: recognition techniques and applications in medical imaging, Pages 1-10.)

Others have described alternative registration techniques including registration of images based on use of a graphics processing unit (GPU). GPU-based processing is known to speed up the time for performing computations. Examples of GPU-based registration are described in U.S. Pat. Nos. 7,483,034 and 7,706,633, both to Chefd'hotel et al. However, in the case of a GPU-based registration, parallelizing the DRR is not enough to speed up the process. Parallelizing the DRR may only result in reducing computational time incrementally, not substantially for 2D-3D deformable registration.

Notwithstanding the above, it is still desirable to develop improved GPU-based registrations techniques. Improved techniques that can perform an accurate 2D to 3D deformable registration on the entire body organ and, at the same time, substantially reduce the computational time of 2D-3D deformable registration.

SUMMARY OF THE INVENTION

Systems and methods for assisting a physician in a medical intervention comprising performing a 2D-3D deformable registration, and more particularly, performing a 2D-3D registration using multiple 2D fluoroscopic views, and implemented on a Graphics Processing Unit.

In embodiments of the present invention, a 3D deformation field is fully recovered. By 'fully recovered', it is meant that the deformation is recovered in 3D space and not just the 2D plane perpendicular to the projection direction using multiple 2D fluoroscopic views. The method uses multiple 2D views "simultaneously" to determine a consistent 3D deformation field which gives more accurate results. Additionally, since the deformation field is computed directly in 3D, the method can accurately handle motion of anatomical structures "overlapping" in 2D images or anatomical structures which are occluded or out-of-view in 2D images.

In other embodiments, just one fluoroscopic view is used or needed for recovering the 3D deformation field but with some uncertainty in the camera viewing direction. The DRR is matched with only one fluoroscopic view in this embodiment.

An advantage of recovering deformation in 3D space is that after registration, the DRR can be directly produced for the navigation even if the camera of the C-Arm is adjusted to other positions (assuming that the fluoroscopic views are acquired at roughly the same breathing level). In contrast, if only the deformation in a 2D space is recovered, a complete registration would have to be repeated each time the camera position of the fluoroscopy unit is changed.

A challenge for recovering 3D deformation lies in the computation complexity and the non-uniqueness of the solution. In embodiments described herein, multiple live 2D fluoroscopic views are used to uniquely define the solution. In other embodiments, the system and the methods are implemented on a GPU for acceleration.

In embodiments, at least two live 2D fluoroscopic views are used to uniquely define the deformation in 3D space. Using two views is preferred over using one view.

In embodiments, a method includes performing a deformable registration using multiple fluoroscopic views at a similar breathing level once, and later using the resulting deformation field to generate a DRR for any camera position.

In embodiments, a method includes performing a deformable registration using at least two fluoroscopic views.

In embodiments, a method includes using one or more combinations of the steps and structures described herein on 3D images at different breathing levels (for example, a 4D CT) to choose the best match.

In embodiments, a method includes a step to separately track rigid patient movement and only recover non-rigid motion using the deformable registration component.

In embodiments, users may choose to use three or more views and the additional view may serve as a backup in case of failure of one of the three views. Further details about view selection may be found in various publications such as, for example, Yao and Taylor, Deformable 2D-3D Medical Image Registration Using a Statistical Model: Accuracy Factor Assessment (American Journal of Science and Engineering, Vol. 1, No. 2, 2012) and Tomaxevic et al, 3D/2D Image Registration: The Impact of X-Ray Views and Their Number (MICCAI, 2007).

For GPU implementation, parallelizing the DRR alone is not enough to significantly speed up computational time. Our goal is to reduce the computational time of 2D-3D deformable registration from hours to seconds.

In embodiments, an improved multi-core processing framework comprises a GPU kernel system. In embodiments, the GPU kernel system includes six GPU kernels constituting two pipelines: a cost pipeline and a gradient pipeline. These two pipelines provide the cost value and the gradient vector, respectively, for an optimizer (e.g., a L-BFGS optimizer residing on the CPU).

In embodiments, a method comprises performing a 2D to 3D deformable registration based on multiple live 2D fluoroscopic views of an object wherein the performing step is implemented, at least in part, on a Graphics Processing Unit (GPU). In embodiments, the method further comprises the step of receiving the multiple live 2D fluoroscopic views of an anatomical structure.

In embodiments, a computer-implemented method for deformably registering 3D image data of a body organ comprising the steps of: a) receiving multiple live 2D fluoroscopic views of the body organ; b) generating, on a multi-core processor, a candidate 3D deformation field based on a plurality of deformation parameters and the 3D image data; c) computing, on the multi-core processor, a cost value wherein the cost value is based on comparing the multiple live 2D fluoroscopic views and multiple candidate virtual 2D fluoroscopic views generated from the candidate 3D deformation field; d) computing, on the multi-core processor, a gradient vector based on the cost value; and e) determining a final 3D deformation field based on the cost value.

In embodiments, the method further comprises adjusting the deformation parameters after the comparing step.

In embodiments, the method further comprises repeating steps b) to d).

In embodiments, the gradient vector is based on the deformation parameters, and the deformation parameters comprise a set of control points.

In embodiments, the method further comprises computing affected regions, in parallel, on a digitally reconstructed radiograph (DRR) for the set of control points.

In embodiments, the body organ is a lung and the medical intervention is a biopsy. The medical intervention can be, at least in part, an endobronchial procedure.

In embodiments, a system for deformably registering 3D CT image data of a patient to live 2D fluoroscopic views of the patient comprising: a first memory location for receiving 3D CT image data of a body organ of the patient; a second memory location for receiving live 2D fluoroscopic views of the patient; a multi-core processor framework that generates a candidate 3D deformation field based on a plurality of deformation parameters and the 3D CT image data; and wherein the multi-core processor framework further optimizes the candidate 3D deformation field based on computing a cost value and a gradient vector based on the cost value; and wherein the multi-core processor framework further selects a final deformation field based on the cost value.

In embodiments, the multi-core processor framework implements a BFGS algorithm to optimize the candidate 3D deformation field.

In embodiments, the multi-core processor framework comprises a CPU and the optimizing is performed on the CPU.

In embodiments, the multi-core processor framework comprises a GPU, and the gradient vector and cost function are computed on the GPU.

In embodiments, the 3D deformation field is modeled as a piece-wise cubic polynomial. The piece-wise cubic polynomial can be a free form deformation.

In embodiments, the deformation parameters comprise a plurality of control points.

In embodiments, the affected areas are computed, in parallel, on the DRR and based on the plurality of control points.

In embodiments, the gradient vector further includes generating a first lookup table for pixel IDs in the affected regions for each control point.

In embodiments, the gradient vector further includes generating a second lookup table for pixel values of the pixel IDs in the affected regions for each control point.

In embodiments, the affected regions are computed based on ray casting.

In embodiments, the multi-core processor is a graphics processing unit (GPU).

In embodiments, the multiple parallel computations comprise computing the multiple affected areas on the DRRs for each control point, and on a GPU.

In embodiments, a non-transitory computer readable medium comprises instructions for carrying out the steps as described herein to perform a deformable 2D to 3D registration.

The description, objects and advantages of the present invention will become apparent from the detailed description to follow, together with the accompanying drawings.

DETAILED DESCRIPTION OF THE INVENTION

Figure 1A:
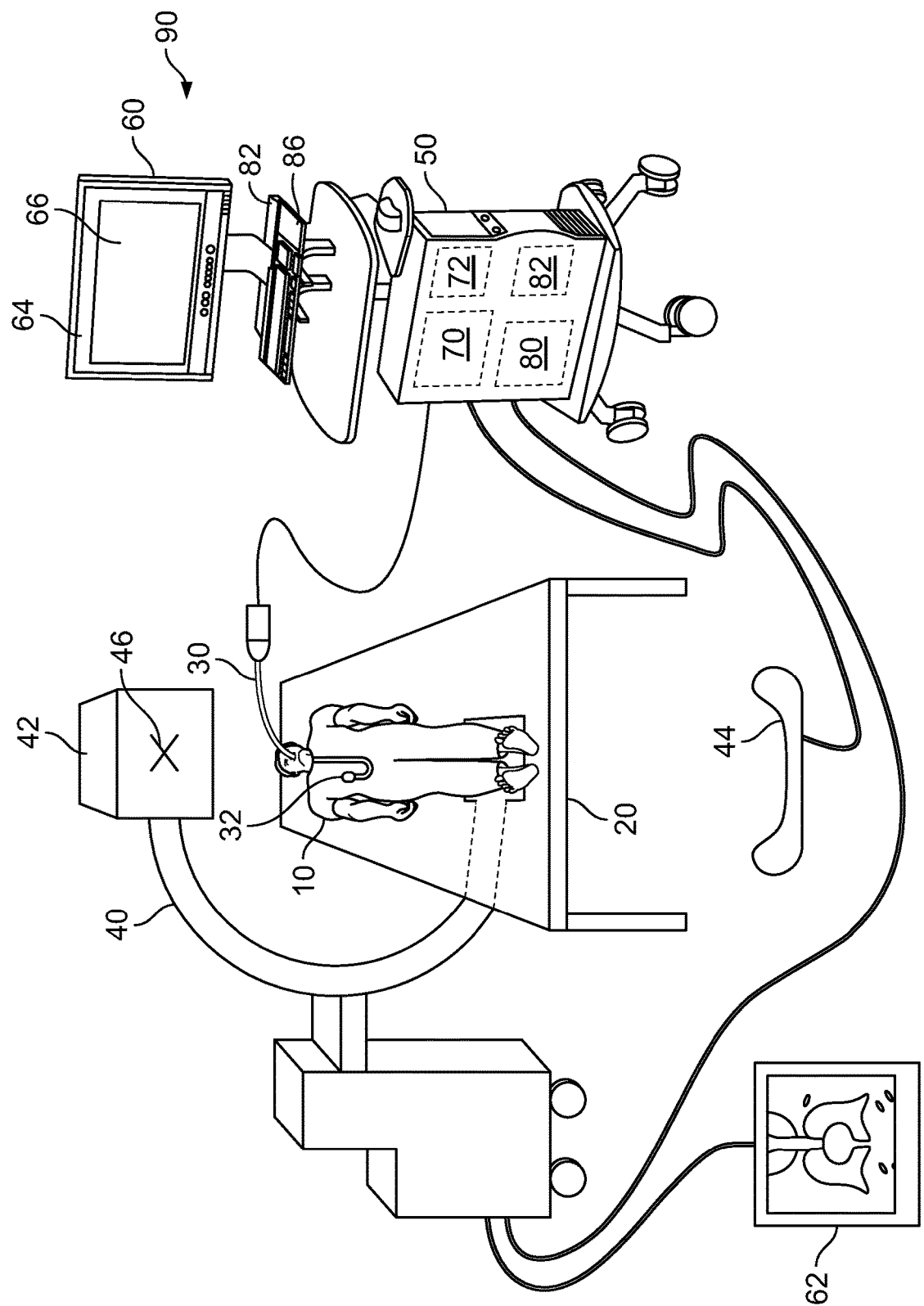
FIG. 1A illustrates an overview of a system for performing a 2D to 3D deformable registration on a patient.

Before the present invention is described in detail, it is to be understood that this invention is not limited to particular variations set forth herein as various changes or modifications may be made to the invention described and equivalents may be substituted without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Last, it is to be appreciated that unless defined otherwise, all technical and scientific terms used herein have the same meaning as commonly understood by one of ordinary skill in the art to which this invention belongs.

Described herein are systems and methods for assisting a physician to perform a 2D-3D deformable registration, and more particular, a 2D-3D registration using multiple 2D fluoroscopic views implemented on a Graphics Processing Unit (GPU), or similar programmable logic chip, or processor, or a parallel architecture.

Overview

FIG. 1A illustrates an overview of a system for performing a 2D-3D deformable registration. In particular, FIG. 1A illustrates a patient or subject 10 on an operating table 20. Although the subject shown in FIG. 1A is a human, the invention is applicable to animals other than humans and may be performed on live or dead animals or subjects as the case may be.

With reference to FIG. 1A, a surgical device 30 is shown positioned and extending into a lung of the subject. The surgical device 30 has a distal working end or tip 32 which has been passed through the subject's mouth, the trachea, a bronchi or more remote airways, and into the lung. While surgical device 30 shown in FIG. 1A is intended to represent an endoscope, namely, a bronchoscope, the invention is not so limited. The surgical device may be a wide range of devices, instruments, implants, and markers which are visible under fluoroscopy, have a portion which is visible under fluoroscopy, or be modifiable such that it is visible under fluoroscopy. Examples, without limitation, include catheters, sheaths, needles, ablation devices, stents, valves, fiducial markers, seeds, coils, etc. In embodiments, a surgical device or tool is advanced into the airways, and then through a wall of the airway towards a region of interest.

A fluoroscope 40 takes real time fluoroscopic video of the subject. Video frames of the video or images are collected or received by workstation 50 for processing. Real time images may also be displayed on a video monitor 62. Examples of the fluoroscope unit, without limitation, are C-Arm, Biplanar fluoroscopy, 3D fluoroscopy, Cone Beam CT, etc.

The location and pose of the fluoroscopy camera 42 is tracked with a tracking sensor 44. In the fluoroscopy unit shown in FIG. 1A, an optically visible symbol 46 is observed by the optical tracking sensor 44 to provide to workstation 50 information about the 3D location and orientation (namely, pose) of the fluoroscopy camera 42 in real time. The optical tracking sensor 44 may be positioned on any fixed surface including the floor, wall, ceiling, or a table. Although the tracking sensor shown in this embodiment is optically based, other techniques (for example, electromagnetic tracking system) to track the camera may be employed and are in accordance with the present invention.

Additionally, the system can work without a tracking mechanism. The 3D camera positions of the fluoroscope relative to each other can be given or computed separately. For example, relative camera positions can be given by the fluoroscope unit itself, or can be computed by performing a rigid 2D-3D registration for each fluoroscopic image separately, or can be computed by observing 2D location of some fixed radio-opaque markers in fluoroscopic images.

Workstation 50, as will be described in more detail below, is configured to receive the fluoroscopy images from the fluoroscopy unit 40 in real-time.

FIG. 1A also illustrates a display 60 showing a plurality of images. As will be described in greater detail herein, workstation 50 is configured to send to the display a number of types of images including 3D model views, 2D model fluoroscopy views, real fluoroscopy views, real endoscopic views, model endoscopic views, and a wide range of information superimposed on the views such as without limitation planning information, region of interests, virtual target markers, vessels, virtual obstacles, real devices, virtual devices, routes to a target, notes and indicia provided by the user, etc.

The workstation 50 shown in FIG. 1A registers the poses shown in the fluoroscopy images from the fluoroscope unit 40 with the 3D location in a 3D model of the subject. As described herein, the information and location may be generated and displayed in a number of ways to the physician to assist tracking the surgical device in real time, and in the event planning information has been provided to the workstation, to guide the physician to a target. Various planning information may be provided or determined by the workstation as described in U.S. Patent Application No. 2008/0183073 to Higgins et al., for example.

As will be discussed in more detail herein, the workstation 50 includes at least one processor 70 (e.g., without limitation, a GPU or other multi-core processing framework) operable to perform a deformable registration in real time based on, amongst other things, the real-time fluoroscopy images.

Workstation 50 is also shown having a memory device 80 which holds or stores information including imaging, device, marker, and procedural data. The memory device may be a hard drive, for example.

The workstation 50 shown in FIG. 1A is adapted to receive real-time images (e.g., fluoroscopy and/or endoscopy images) through various input ports or connectors (e.g., USB port, video port, etc.). A frame grabber card 72 captures individual video frames or images for processing. Real time fluoroscopy images may be obtained by the workstation 50, for example, from continuous fluoroscopy video, video clips, and/or still frames. The workstation is further adapted to send image data to a display using a video card 82. An example of a workstation is a Dell Computer Precision T5500 T5400, with Dual-core Intel Xeon 2.67 GHz processor, and a Nvidia GeForce GTX TITAN BLACK.

The system 90 shown in FIG. 1A also includes a display 60 which may present reports, data, images, results and models in various formats including without limitation graphical, tabular, and pictorial form. In one embodiment of the present invention, a surgical device is superimposed on a 3D model of the organ.

It is to be understood, however, that although the system in FIG. 1A is shown with a memory 80 for receiving and storing various information the invention is not so limited. In an alternative embodiment the system may be configured to merely access a memory device such as a USB stick, a CD, or other media storage device.

The system 90 shown in FIG. 1A also includes a user input device 86 such as, for example, a keyboard, joystick, or mouse. The user input device allows a user such as the physician to add or input data and information as well as modify planning information and to make notes in the files and records.

Figure 1B:
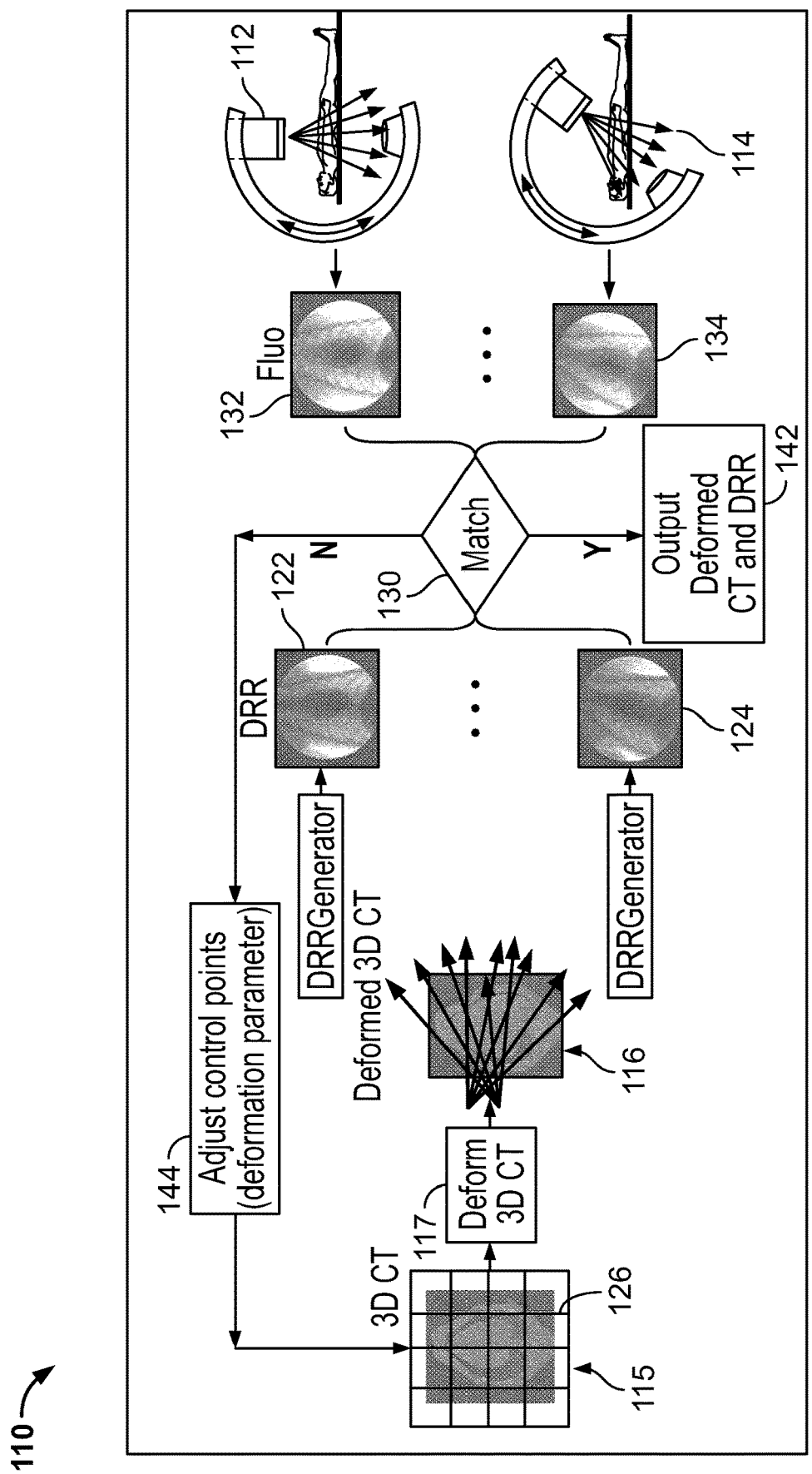
FIG. 1B illustrates an overview of a method for performing a 2D to 3D deformable registration. The 3D CT is manipulated by a set of control points or deformation parameters (e.g., a 3D Free-Form control points.) DRRs are generated based on the deformed 3D CT to produce DRRs for multiple views. The multiple view DRRs are compared to the multiple fluoroscopic images. If a match is reached, the deformed 3D CT is output. Otherwise, the control points are adjusted to deform the 3D CT image. And the process is repeated.

FIG. 1B illustrates an overview of a method 110 for 2D-3D registration of the lung using multiple fluoroscopic views 112, 114. 3D image data 115 of a patient's lung is deformed 117 to produce a candidate deformed 3D image 116 based on a grid of control points 126. The 3D image data 115 may include, for example, preoperative image data arising from CT, MRI, or other means.

Multiple DRRs are created 122, 124 from the deformed 3D image data 116.

Next, and as will be described in more detail herein, the DRRs 122, 124 are compared 130 to the multiple fluoroscopic images 132, 134.

When comparing a virtual fluoroscopic 2D image or the DRR with its candidate live fluoroscopic image, the DRR is produced according to the recorded view angle from the fluoroscope as discussed above in connection with FIG. 1A. The view angle between the successive view and the first view may be obtained by a tracking tool 46 fixed on the C-Arms of the fluoroscope. An example of tracking and calibrating the fluoroscope is described in US Patent Publication Nos. 20120289825 and 20120288173, both to Rai et al.

If the images match, the deformed CT and the DRRs are output 142. Otherwise, (e.g., if the images do not match to a desired level of accuracy), the control points 126 are adjusted 144 to deform the 3D image data.

Registering Multiple Fluoroscopic Images

In embodiments, the step matching or comparing the multiple fluoroscopic images to a 3D image data comprises determining the 3D deformation field U.

In embodiments, the 3D deformation field U is solved as an optimization problem comprising the step of computing a cost function. The following is an example of a cost function:

$$J(CT, Fluo, U) = \text{Metric}(DRR(U(CT)), Fluo) \quad (1)$$

in which, the CT represents a 3D CT image, Fluo represents one big fluoroscopic image constituted by putting the fluoroscopic images one after another. The U is the unknown deformation field. U(CT) represents the deformed CT. DRR represents a big DRR constituted by putting the DRR at different views one after another. DRR may be produced by a ray casting method, quite similar with CT imaging. It is also possible to add additional constraints in (1) on the deformation field T which may be based on properties of anatomical tissues in the 3D image. Examples of such anatomical properties, without limitation, include rigidity of spinal column, ribs, and lung tissues.

For the Metric, to match DRR with Fluo, we can use the normalized cross-correlation (NCC) since it works well in the same modality registration, $$\frac{\sum_{i,j}(DRR(i,j) - \overline{DRR})(Fluo(i,j) - \overline{Fluo})}{\sqrt{\sum_{i,j}(DRR(i,j) - \overline{DRR})^2 \sum_{i,j}(Fluo(i,j) - \overline{Fluo})^2}} \quad (2)$$

in which, $\overline{DRR}$ means the average intensity of DRRs and $\overline{Fluo}$ means the average of fluoroscopic images.

In one preferred GPU implementation of the cost and the gradient, the standard NCC equation (2) is adapted accordingly to suit the GPU implementation.

In embodiments, the deformation is modeled as a Free-From Deformation (FFD), which is a piece-wise cubic polynomial. (Lee S, Wolberg G, Shin S Y. Scattered data interpolation with multilevel B-splines. IEEE Transactions on Visualization and Computer Graphics 2002: 3: 228-44.) FFD can be manipulated by a regular control grid with spacing $s_x \times s_y \times s_z$ for a 3D image. FFD is computationally efficient, because the deformation at any point is only influenced by its surrounding 4×4×4 control points.

For a point p with coordinate (x, y, z), assume its 4×4×4 control points are $p_{ijk}$, i, j, k=0 ... 3. Denote $d_{ijk}$ as the displacement vector associated with the control point $p_{ijk}$, the displacement at point p is defined as, $$U(x, y, z | d_{ijk}) = \sum_{i=0}^{3}\sum_{j=0}^{3}\sum_{k=0}^{3} B_i(u)B_j(v)B_k(w) \quad (3)$$

where $$u = \frac{x}{s_x} - \lfloor\frac{x}{s_x}\rfloor, \; y = \frac{y}{s_y} - \lfloor\frac{y}{s_y}\rfloor, \; w = \frac{z}{s_z} - \lfloor\frac{z}{s_z}\rfloor.B_i, \; i=1,2,3$$

is the i-th basis function of Bsplines. (Lee S, Wolberg G, Shin S Y. Scattered data interpolation with multilevel B-splines. IEEE Transactions on Visualization and Computer Graphics 2002: 3: 228-44.)

We can denote the vector U as the concatenation of $d_{ijk}$.

Cost function (1) is optimized by a L-BFGS optimizer, which believed to be more efficient compared to a simple gradient descent optimizer for high dimensional optimization problems. See, for example, Nocedal J and Wright S J. Numerical optimization. New York: Springer Verlag; 1999: 221-26.

L-BFGS is a gradient-based optimizer. Both the gradient and cost are needed in the optimizer. For the cost function (1), the gradient is calculated analytically since the image, the deformation and the DRR projection can be represented analytically. Various methods may be used to calculate the gradient. An exemplary method to calculate the gradient is, for example, center differencing. Ames, W. F., (1977). Numerical Methods for Partial Differential Equations, Section 1.6. Academic Press, New York. ISBN 0-12-056760-1.

GPU Implementation

In embodiments a GPU implementation of 2D-3D deformable registration uses OpenCL1.1 on GeForce GTX TITAN Black GPU (manufactured by Nvidia Corporation, Santa Clara, Calif.). OpenCL1.1 is a computer language for GPU and described in, for example, John E. Stone, David Gohara, and Guochun Shi. 2010. OpenCL: A Parallel Programming Standard for Heterogeneous Computing Systems. IEEE Des. Test 12, 3 (May 2010), 66-73.

Figure 2:
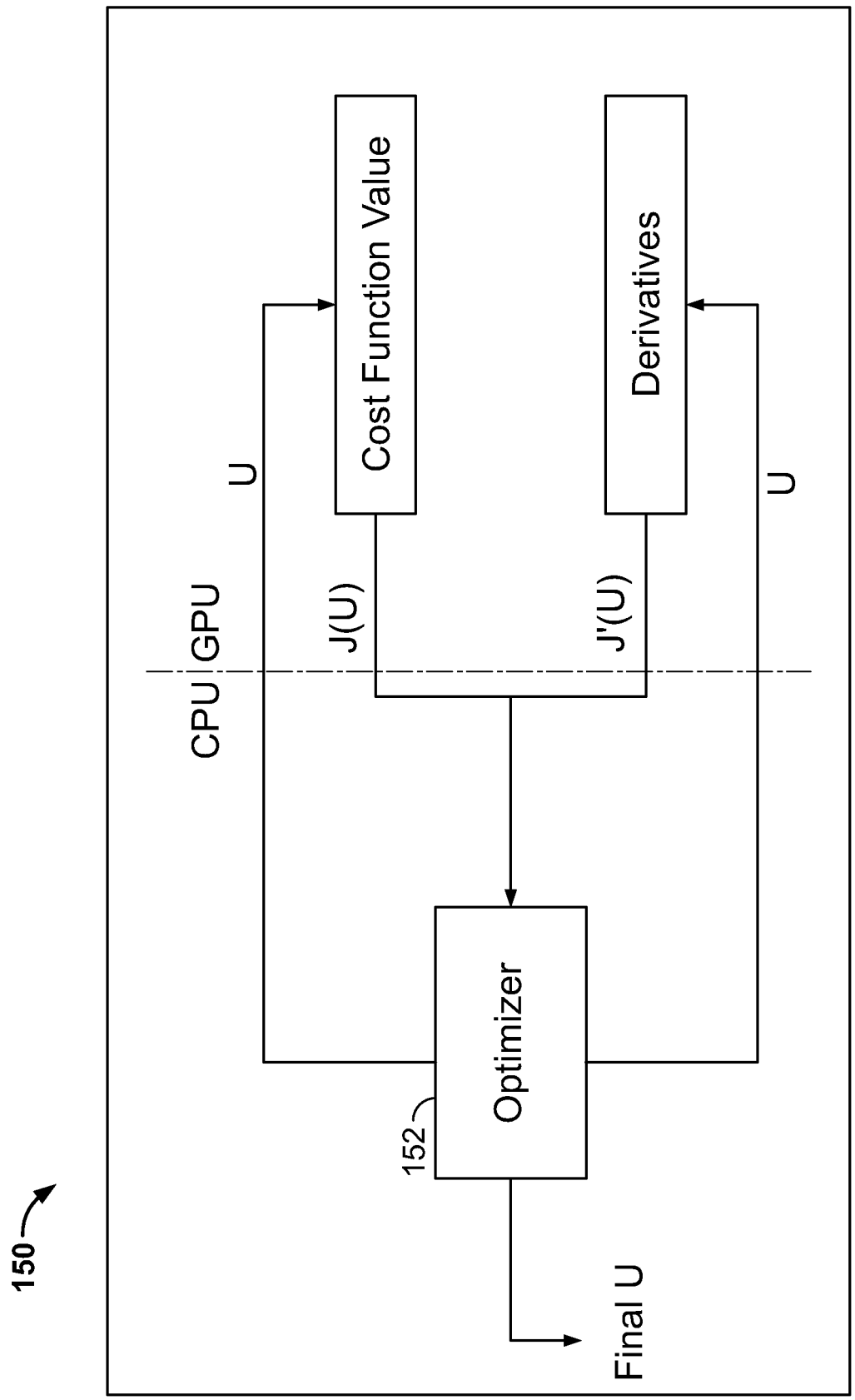
FIG. 2 illustrates a framework of GPU implementation of the 2D-3D deformable registration.

FIG. 2 shows a framework 150 of the implementation, in which the optimizer 152 (e.g., L-BFGS optimizer) receives a cost value (shown as J(U)) and the gradient vector (shown as J'(U)) to determine a next step. As mentioned herein the calculation of the cost and the gradient is extremely computationally intensive. Use of the GPU serves to speed up the time for computation.

Figure 3:
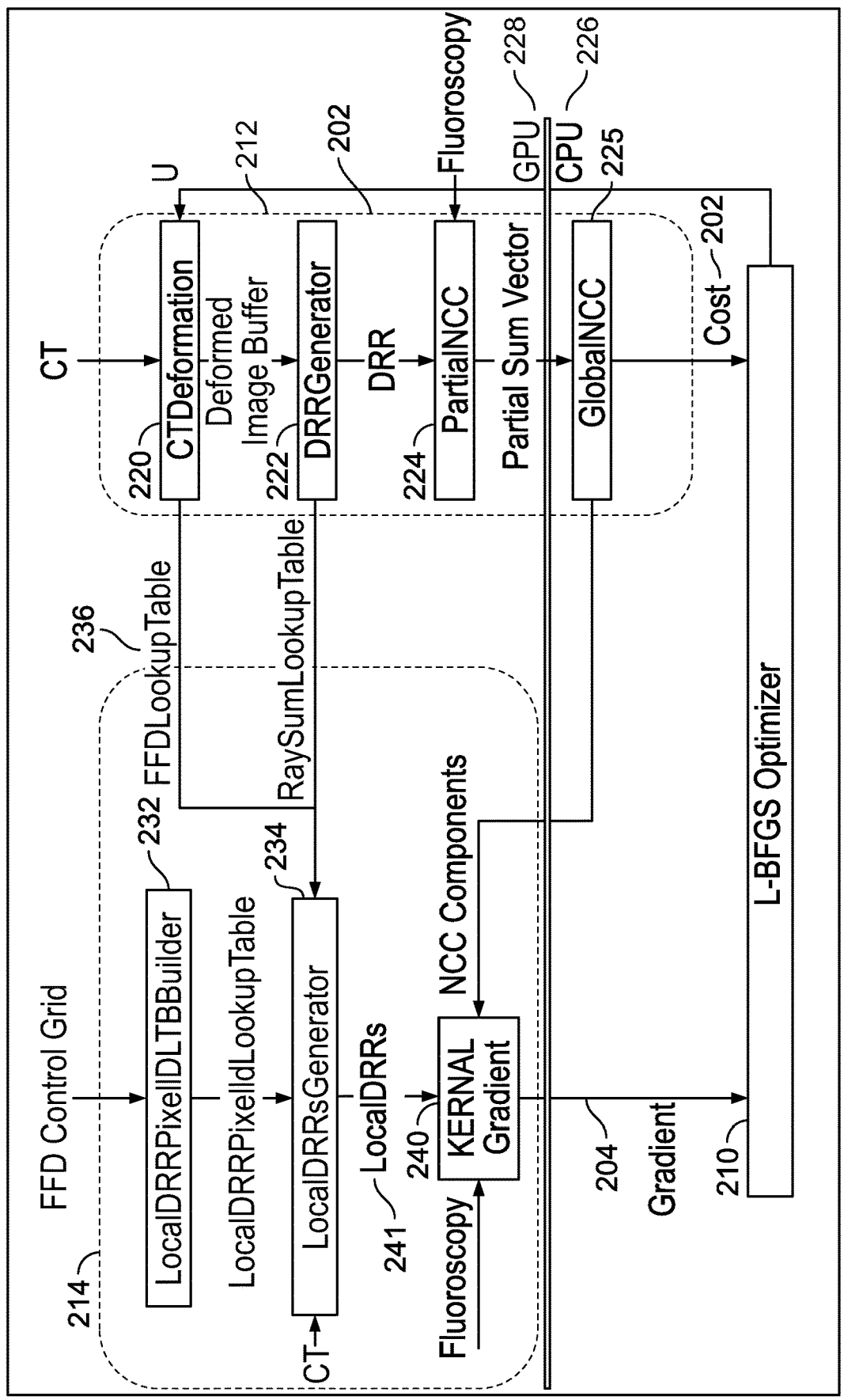
FIG. 3 illustrates a Kernel system including two kernel pipelines: a cost pipeline and a gradient pipeline.

FIG. 3 illustrates a GPU implemented framework 200 to compute the cost 202 and gradient 204. As shown the system includes a CPU 226 and GPU 228.

The cost value 202 may be calculated using a series of steps (namely, the cost pipeline 212). The gradient is calculated using another series of steps (namely, the gradient pipeline 214).

Cost Pipeline

FIG. 3 shows an embodiment to carry out the cost pipeline 202 including the following steps: deforming the CT image (220), generating the DRR (222), calculating the partial sum (224), and calculating the final sum (225). As shown in this embodiment, many of the steps can be performed on a GPU 228, and the step of calculating the final sum can be performed on a CPU (226).

In the deforming step 220, the CT image is deformed 220 according to the current deformation field U. This step 220 may be carried out by a program or kernel as described in, for example, Modat, Marc et al., Fast free-form deformation using graphics processing units, Computer Methods and Programs in Biomedicine, Volume 98, Issue 3, 278-284.

In the generating step 222, the DRR is generated. A program or DRRGenerator kernel may be used to produce the DRR based on the deformed image as described in, for example, Tornai G J, Cserey G, Pappas I, Fast DRR generation for 2D to 3D registration on GPUs, MedPhys. 2012 August; 39(8):4795-9. doi: 10.1118/1.4736827.

Next, the partial sum is computed by a program or kernel 224. The inputs of this program are the DRR and the Fluoroscopy, and the output is the Partial sum vector. In embodiments, the kernel proceeds as follows: load the DRR and Fluoro into global memory; load the DRR and Fluoro into share memory; in a loop, calculate the sum for one pair in a binary fashion; and output the result of each group to the global memory.

More specifically, the partial sum may be computed using an applicable normalized cross correlation. The applicable normalized cross correlation (NCC) is:

$$\frac{\sum_{i,j}(DRR(i,j) \times Fluo(i,j)) - \overline{Fluo}\sum_{i,j}DRR(i,j) - \overline{DRR}\sum_{i,j}Fluo(i,j) + n \times \overline{DRR} \times \overline{Fluo}}{\left(\sum_{i,j}DRR(i,j)^2 - 2\overline{DRR}\sum_{i,j}DRR(i,j) + n \times \overline{DRR}^2\right)\left(\sum_{i,j}Fluo(i,j)^2 - 2\overline{Fluo}\sum_{i,j}Fluo(i,j) + n \times \overline{Fluo}^2\right)} \quad (4)$$

In equation (4), there are five different summation operations, which can be implemented using GPU reduction operations (Mark Harris, Optimizing Parallel Reduction in CUDA, NVIDIA Developer Technology, http://developer.download.nvidia.com/compute/cuda/1.1-Beta/x86_website/projects/reduction/doc/reduction.pdf). In embodiments an 8-component vector is employed. The first 5 components are used to store the summations.

Preferably, the reduction on the 8-component vector is performed only once. In GPU reduction, the vector will be divided into array size/work-group size parts. Each thread group is responsible for the summation of its corresponding part. For instance, if the vector size is 256×256, after reduction, the output is a 256 vector with each component storing a partial summation.

Global synchronization can be performed using the kernel call. For example, after kernel PartialINCC 224, the array size/work-group size partial results will appear in GPU 228 global memory. These partial results may be fed into the CPU 226 to finish the final summation. The cost value 202 is sent to L-BFGS optimizer 210. Some intermediate results of the NCC are sent to the gradient pipeline for incremental calculation of the cost in the gradient calculation, as described herein.

Gradient Pipeline

As mentioned above, one algorithm to calculate the gradient 204 is central differences. For simplicity, in the following, we only consider the derivative along x direction:

$$J_x = (J(x+\Delta x) - J(x-\Delta x))/2\Delta x$$

In an embodiment, each GPU thread calculates the derivative for one control point. Each thread can invoke the cost pipeline twice with small disturbance along positive x and negative x directions, respectively.

Each thread can hold a global memory to store the DRR, and consequently a large amount of memory needed. Also, the computation for one thread to calculate the cost is heavy.

In another embodiment, in each thread, not all the DRR is stored nor is the cost calculated from scratch.

A program or kernel 240 may be employed to carry out the above described steps and implemented on GPU 228. For example, a Kernel Gradient 240 may perform the following steps: Loop the local DRR region to incrementally calculate the NCC along positive (+) x direction 241; Loop the local DRR region to incrementally calculate the NCC along negative (−) x direction 241; Use central differences to calculate the derivative; and Output the gradient vector 204 to CPU 226.

Figure 4A:
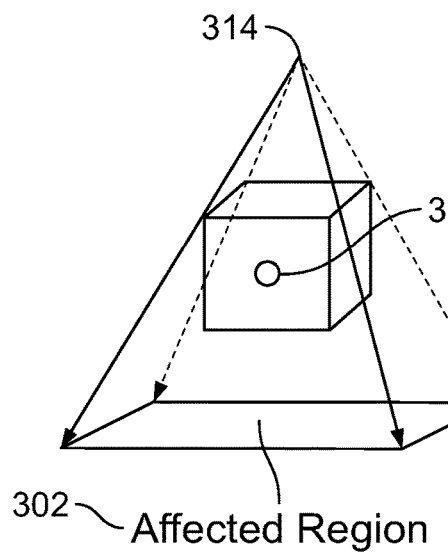
FIG. 4a illustrates an affected region in the DRR after the change of one control point.

FIG. 4a illustrates an affected region 302 of the DRR if one control point is changed. The white point 310 represents a control point. A small disturbance Δx of this control point will affect its surrounding region covered by a 5×5×5 control points. Some pixels in the DRR will be affected if the ray connecting the DRR pixel and the source 314 intersects the cubic. Thus, for one thread, it does not need to store the entire DRR. This thread preferably only stores the affected region indicated by reference numeral 302. Along with an original DRR shared by all threads, this thread can have a complete DRR after the voxels inside the cube are changed.

To store the pixels inside the affected region after DRR generation, we first prefer to know which pixels are inside the region.

In embodiments a lookup table for each control point may be built, in which each entry records the pixel Id of the DRR. This table does not change in the whole optimization procedure. It only needs to be calculated once. For example, the kernel LocalDRRPixelIDLTBBuilder can perform this task.

In the Kernel LocalDRRPixelIDLTBBuilder, the input is the FFD control points and the output is a lookup table recording the DRR pixel ID in the affected region. The kernel proceeds as follows: find the 5×5×5 region in 3D CT space; determine if the ray is intersected with the region or not; and use a gather operation to record all DRR pixel IDs for each 5×5×5 region.

Figure 4B:
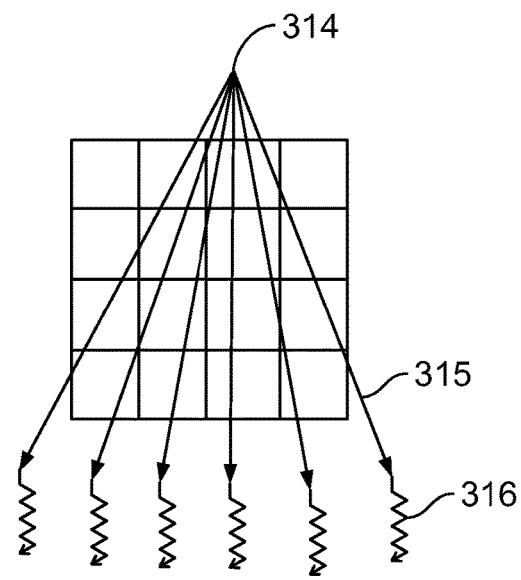
FIG. 4b illustrates parallel granularity for the kernel LocalDRRPixelIDLTBBuilder and LocalDRRsGenerator.

FIG. 4b illustrates for this kernel parallel granularity on the ray level. The global thread size is equal to the number of rays or the DRR size. Each thread 316 corresponds with one ray 315. For each thread 316, it loops over all cubes to check which cube it intersects. And, for each cube, all rays intersecting with it will be recorded by a gather operation.

Without being bound to theory, parallelizing on the ray level is desirable because the size of the DRR is much larger than the number of cubes. Parallelizing (namely, performing parallel computations) on the ray level can dramatically reduce the burden of the kernel, which is favored by multi-core processing frameworks such as, for example, a GPU. GPU-based frameworks are well suited for, amongst other things, simultaneously running numerous simple tasks rather than a few complex tasks.

With reference again to FIG. 3, a kernel 232 (e.g., Kernel LocalDRRPixelIDLTBBuilder) records the affected DRR pixel Id for each control point.

A kernel 234 (e.g., Kernel LocalDRRsGenerator) calculates the DRR pixel value for each control point in parallel. The inputs of this kernel are the LocalDRRPixelIdLookupTable, FFDLookupTable 236 and RaySumLookupTable and CT, and the output is the LocalDRRs 241, which record the updated DRR pixels for all 5×5×5 region. Steps for this kernel are as follows: get the pixel Id from LocalDRRPixelIdLookupTable; for all samples on the ray inside the 5×5×5 region, tri-linear interpolation the intensity based on the FFDLookupTable and the CT; update the sum of the samples on the ray inside the 5×5×5 region and then update the RaySumLookupTable; and generate updated DRR (local DRR) for each 5×5×5 region.

The kernel is launched as the LocalDRRPixelIDLTBBuilder with the same parallel granularity. Each thread will redo the ray casting, and all DRR pixels corresponding with the control point will be collected by a gather operation. In this kernel, the tri-linear interpolation is performed, which is facilitated by a pre-computed lookup table: FFDLookupTable, an intermediate result of kernel CTDeformation Since only part of the DRR is affected after the disturbance of one control point. An incremental method can be used to update the NCC instead calculating it from scratch.

To reach the incremental calculation, the original NCC equation is derived as:

$$\frac{\sum_{i,j}(DRR - \overline{DRR} + \Delta\overline{DRR})(Fluo - \overline{Fluo})}{\sqrt{\sum_{i,j}(DRR - \overline{DRR} + \Delta\overline{DRR})^2 \sum_{i,j}(Fluo - \overline{Fluo})^2}} \rightarrow \quad (5)$$

$$\frac{\sum_{i,j}(DRR - \overline{DRR})(Fluo - \overline{Fluo})}{\sqrt{\sum_{i,j}((DRR - \overline{DRR})^2 + \Delta\overline{DRR}^2) \sum_{i,j}(Fluo - \overline{Fluo})^2}}$$

in which, $\overline{DRR}$ is the original mean of DRR before we change the control point, and $\Delta\overline{DRR}$ is the change of the mean after the control point is changed.

From equation (5), except the term $\Delta\overline{DRR}$, all the other terms are available after the cost pipeline.

Figure 4C:
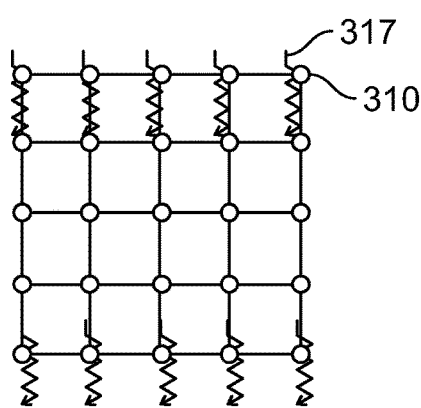
FIG. 4c illustrates parallel granularity for the kernel Gradient.

So, in the kernel Gradient 240, we can first loop the small affected region, output by kernel DRRGenerationForGradient, to get the sum of the changed DRR pixels and then combine with the original mean and the number of the pixels, we can calculate $\Delta\overline{DRR}$. After $\Delta\overline{DRR}$ is obtained, along with other terms sent from CPU, we can directly calculate the updated NCC after the change of the control point. Repeating the above procedures along positive x and negative x, respectively, we can get corresponding NCC, and then use central differences to calculate the derivative. With reference to FIGS. 4A-4C, the kernel Gradient is launched at the control point 310 level. Each thread 317 is responsible for the calculation of the derivative of one control point 310. The parallel granularity is illustrated in FIG. 4c.

The gradient difference and pattern intensity metrics provides more robust and accurate in 2D-3D registration than some alternative metrics. This is supported in the literature. See, for example, Penney, G., Weese, J., Little, J. A., Desmedt, P., Hill, D. L., Hawkes, D. J., 1998. A, comparison of similarity measures for use in 2-D-3-D medical image registration. IEEE Transactions on Medical Imaging 17, 586-595. The Gradient kernel 240 is independent of the LocalDRRsGenerator 234 kernel. Therefore, only the Gradient kernel 240 needs to be modified if another metric is introduced.

In another embodiment, a non-transitory computer readable medium includes a set of instructions for use with a computer to carry out any one or combination of the steps, functions, and methods described herein. In another embodiment, a GPU includes a set of instructions to carry out any one or combination of the steps, functions, and methods described herein.

While preferred embodiments of this disclosure have been shown and described, modifications thereof can be made by one skilled in the art without departing from the scope or teaching herein. The embodiments described herein are exemplary only and are not intended to be limiting. Because many varying and different embodiments may be made within the scope of the present inventive concept, including equivalent structures, materials, or methods hereafter thought of, and because many modifications may be made in the embodiments herein detailed in accordance with the descriptive requirements of the law, it is to be understood that the details herein are to be interpreted as illustrative and not in a limiting sense.

We claim:

1. A system for deformably registering pre-acquired 3D CT image data of a patient to real time 3D data of the patient comprising:
    a first memory for receiving 3D CT image data of a body organ of the patient;
    a second memory for receiving real-time image data of the patient from an imaging unit;
    a multi-core processor framework that generates a candidate 3D deformation field based on one or more deformation parameters and the 3D CT image data; and
    wherein the multi-core processor framework is further operable to compute a cost function and gradient vector to determine an optimal deformation field; wherein the cost function is based on the candidate 3D deformation field and the real time image data; and the gradient vector is based on the cost function.

2. The system of claim 1, further comprising the imaging unit.

3. The system of claim 2, wherein the imaging unit is one selected from the group consisting of a C-Arm, Biplanar fluoroscopy, 3D fluoroscopy, and Cone Beam CT.

4. The system of claim 1 wherein the multi-core processor framework comprises a CPU and GPU, and the optimizing step is performed on the CPU.

5. The system of claim 1 wherein the multi-core processor framework comprises a GPU, and the computation of the cost function and gradient vector are performed on the GPU.

6. The system of claim 5 wherein the multi-core processor framework is operable to implement a BFGS algorithm to optimize the candidate 3D deformation field.

7. The system of claim 4 comprising computing, in parallel, affected regions of the pre-acquired 3D data for a plurality of control points.

8. The system of claim 7 wherein the gradient vector further includes generating a first lookup table for pixel IDs in the affected regions for each control point.

9. A computer-implemented method for assisting a physician in a medical intervention on a patient comprising:
    receiving pre-acquired 3D image data of a body organ of the patient prior to the medical intervention;
    receiving real-time image data of the body organ; and
    performing, on a multi-core processing framework, multiple parallel computations to determine a deformable registration on the pre-acquired 3D image data and the real-time data from the receiving step, and wherein the multi-core processing framework computes a 3D deformation field; and
    wherein the performing step includes computing a cost function value and a gradient vector to determine the deformable registration on the pre-acquired 3D image data.

10. The method of claim 9 comprising inputting the cost function value and the gradient vector into an optimizing algorithm.

11. The method of claim 10 comprising computing, in parallel, affected regions of the pre-acquired 3D data for a plurality of control points.

12. The method of claim 11 wherein the gradient vector further includes generating a first lookup table for pixel IDs in the affected regions for each control point.

13. The method of claim 9 wherein the multiple parallel computations are carried out on a graphics processing unit (GPU).

14. The method of claim 10 wherein the optimizing algorithm is limited-memory BFGS based.

15. The method of claim 9 wherein the performing step is carried out in less than 30 seconds.

16. The method of claim 9, wherein the receiving real time 3D data of the body organ is carried out with a unit for obtaining images.

17. The method of claim 16, wherein the unit for obtaining imaging is one selected from the group consisting of a C-Arm, Biplanar fluoroscopy, 3D fluoroscopy, and Cone Beam CT.

* * * * *